United States Patent
Moghe et al.

(10) Patent No.: US 8,687,871 B2
(45) Date of Patent: Apr. 1, 2014

(54) IMAGE DOMAIN BASED NOISE REDUCTION FOR LOW DOSE COMPUTED TOMOGRAPHY FLUOROSCOPY

(75) Inventors: Sachin Moghe, Northbrook, IL (US); Ilmar Hein, Chicago, IL (US)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/557,467

(22) Filed: Jul. 25, 2012

(65) Prior Publication Data

US 2012/0294417 A1 Nov. 22, 2012

Related U.S. Application Data

(63) Continuation of application No. 12/539,674, filed on Aug. 12, 2009, now abandoned.

(51) Int. Cl.
*A61B 6/03* (2006.01)
(52) U.S. Cl.
CPC ............. *A61B 6/03* (2013.01); *Y10S 378/901* (2013.01)
USPC .............................. 382/131; 378/4; 378/901
(58) Field of Classification Search
USPC ................... 378/4, 901; 382/128–132
See application file for complete search history.

(56) References Cited

U.S. PATENT DOCUMENTS

| 5,594,767 | A | * | 1/1997 | Hsieh ................................ 378/8 |
| 5,907,593 | A | | 5/1999 | Hsieh et al. |
| 6,400,789 | B1 | * | 6/2002 | Dafni ............................. 378/15 |
| 6,970,585 | B1 | * | 11/2005 | Dafni et al. .................. 382/131 |
| 7,006,592 | B2 | | 2/2006 | Ali et al. |
| 7,164,745 | B2 | | 1/2007 | Tsuyuki |
| 2009/0052727 | A1 | * | 2/2009 | Eusemann et al. ............ 382/100 |

FOREIGN PATENT DOCUMENTS

JP 11-009589 1/1999

OTHER PUBLICATIONS

Office Action issued Feb. 4, 2014, in Japanese Patent Application 2010-181051 (with English-language translation).

* cited by examiner

*Primary Examiner* — Toan Ton
*Assistant Examiner* — John Corbett
(74) *Attorney, Agent, or Firm* — Oblon, Spivak, McClelland, Maier & Neustadt, L.L.P.

(57) ABSTRACT

A method of computed-tomography and a computed-tomography apparatus in which x-ray projection data is acquired at a number of views for a scan of an object. Partial images are created from data for a desired number of said views. Full scan images are created from plural ones of the partial images. Non-overlapping time images are created from the full-scan images. Gradient images are also created. An improved image is created by weighting respective ones of the full scan and non-overlapping time images using the gradient image. The improved image has increased sharpness with reduced noise.

21 Claims, 9 Drawing Sheets

IMAGE DOMAIN BASED NOISE REDUCTION FOR LOW DOSE COMPUTED TOMOGRAPHY FLUOROSCOPY

CROSS REFERENCE TO RELATED APPLICATION

This application is a Continuation of and claims the benefit of priority under 35 U.S.C. §120 from U.S. Ser. No. 12/539,674, filed Aug. 12, 2009, the contents of which are incorporated herein by reference.

BACKGROUND OF THE INVENTION

1. Field of the Invention

The present invention relates to reducing noise in computed tomography (CT) images during CT-fluoroscopy.

2. Discussion of the Background

CT-fluoroscopy involves continuous scanning of a slice or volume of a subject for monitoring in real time, such as monitoring interventions. If a regular dose of x-rays is used, the subject will be exposed to a large x-ray dose. If a lower dose is used, then image noise is increased. In CT, image noise is inversely proportional to the square root of the x-ray tube current. As the tube current is decreased to reduce dose, the image noise increases, resulting in poor image quality. One method used to reduce image noise is to average the image slices at the same location, but this produces blurring of the edges since there is bound to be movement of the subject, voluntary or involuntary, during the scan. For example, involuntary motion can be due to breathing or beating of the heart.

SUMMARY OF THE INVENTION

One aspect of the present invention is a computed-tomography method including exposing an object with x-rays at a plurality of scans at a position of the object to obtain projection data at a plurality of views, defining a group of views, where each scan includes a first number of the groups, generating first images respectively using projection data from each group of views, generating second images from plural ones of the first images, generating third images by averaging respective pluralities of the second images, generating a gradient image using at least one of the second and third images, and generating a display image by weighting one the of second images and one of the third images using the gradient image.

In another aspect of the invention, a computed-tomography apparatus includes an x-ray source to expose an object with x-rays at a plurality of scans at a position of the object to obtain projection data at a plurality of views, an x-ray detector, a data collection unit, a data processing unit connected to the data collection unit, and a display. The data processing unit includes a memory storing x-ray projection data for a plurality of scans at a position of an object to obtain projection data at a plurality of views, and the data processing unit generates first images respectively using projection data from each group of views, generates second images from plural ones of the first images, generates third images by averaging respective pluralities of the second images, generates a gradient image using at least one of the second and third images, and generates a display image on the display by weighting one the of second images and one of the third images using the gradient image.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
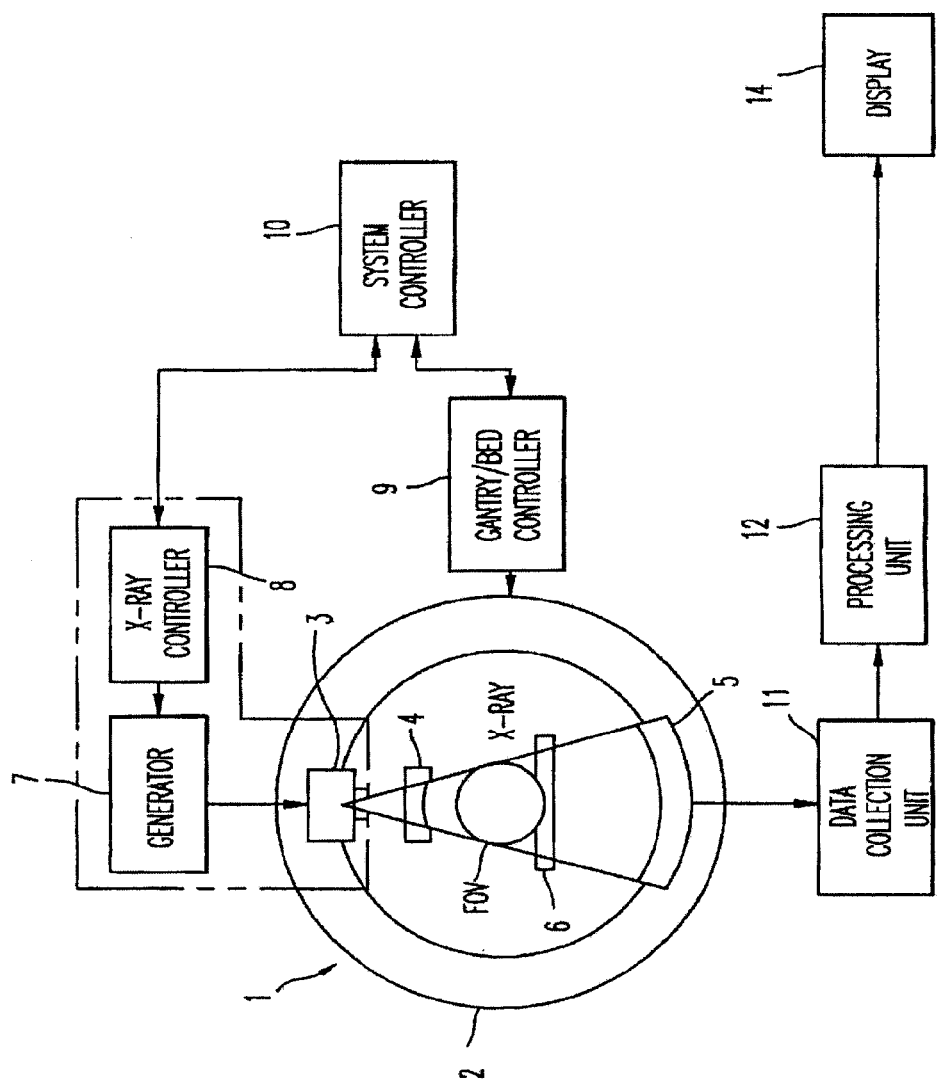
FIG. 1 is a diagram of a system according to the invention.

FIG. 1 shows an x-ray computed tomographic imaging device according to the present invention. The device may be operated as different x-ray doses to carry out different types of scanning, such as CT fluoroscopy. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3. The source may also be scanned circularly.

The output signal of two-dimensional array type x-ray detector 5 is amplified by a data collection unit 11 for each channel and converted to a digital signal, to produce projection data. The projection data output from data collection unit 11 is fed to processing unit 12. Processing unit 12 performs various processing using the projection data. Unit 12 performs interpolation, backprojection and reconstruction. Unit 12 determines backprojection data reflecting the x-ray absorption in each voxel. In the helical scanning system using a cone-beam of x-rays, the imaging region (effective field of view) is of cylindrical shape with radius o) (is there a word missing here?) centered on the axis of evolution. Unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 2:
FIG. 2 is a matrix of views collected over one rotation of the x-ray source.

In typical CT operation, projection data is collected over one rotation of the x-ray source (full scan). The number of views collected per rotation in time ($T_{Rot}$) is $N_{VPR}$, and during each view, data is collected from a set of detectors $N_d$. There may be one or more rows of detectors. For ease of explanation, a detector with one row is considered. The views collected over one rotation can be represented as a matrix shown in FIG. 2. Each cell in the matrix represents a sample of the data collected at any given view (y-axis) and any given channel (x-axis).

Figure 1A:
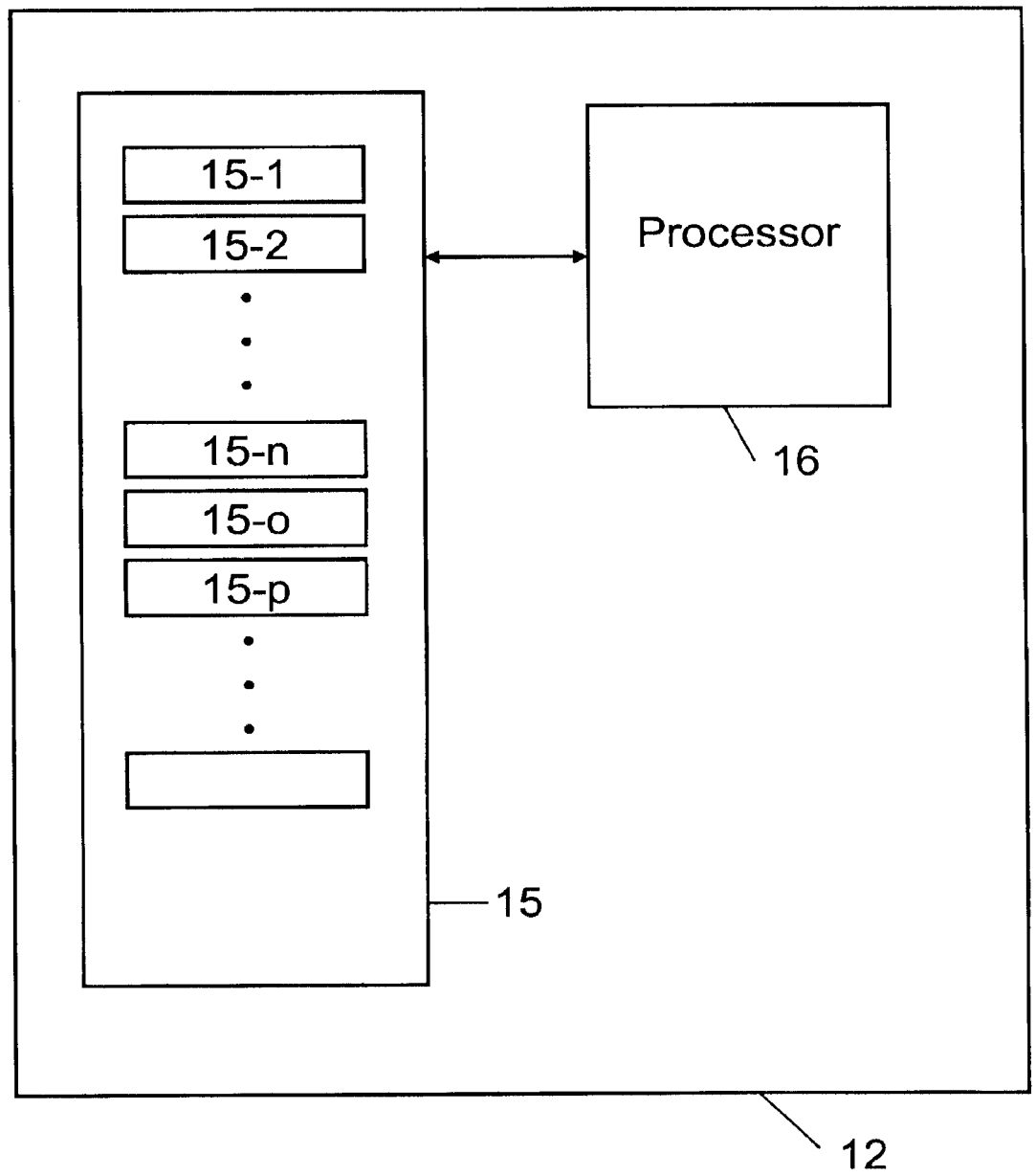
FIG. 1A is a diagram of the processing unit of FIG. 1.

A more detailed view of collection unit 11 and processing unit 12 is shown in FIG. 1A. The projection data is collected and the data for each of a desired number of views is stored in a register or portion of memory unit 11-1 to 11-n. FIG. 1A will be described in more detail below.

For CT fluoroscopy, the same slice position is scanned repeatedly for more than one rotation ($N_{Rot}$). The total number of views collected is given by $N_{Rot}|N_{VPR}$ compared with just $N_{VPR}$ in the case of typical CT operation. Since there is a continuous feed of the views, it is not necessary to wait until the end of an integral number of $T_{Rot}$ to reconstruct an image. A real time image may be reconstructed using data views equal to $N_{VPR}$ at any given time (the views are counted backwards from any point in time). Preferably, real-time images are reconstructed at a desired fraction of the rotation, such as every ¼ or ⅙ rotation.

Figure 3:
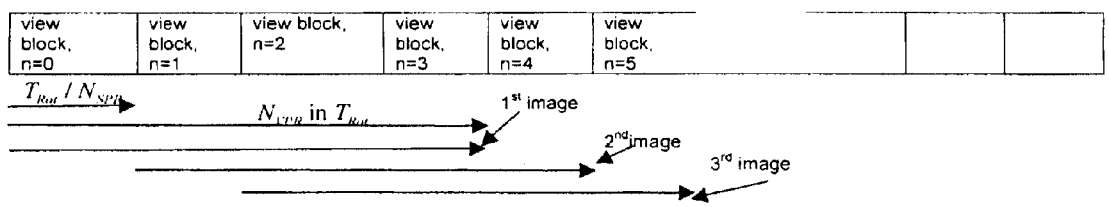
FIG. 3 is a diagram of view blocks and image reconstruction over the view blocks.

FIG. 3 illustrates an example with the number of sections per rotation $N_{SPR}=4$. An image may be reconstructed every $T_{Rot}/N_{SPR}$. As an example, for a rotation time $T_{Rot}=1$ sec, an image may be produced every 0.25 sec. This provides an effect similar to real-time image production or CT fluoroscopy. In FIG. 3, while $N_{SPR}=4$, it can take on other values such as 6 or 8. The higher the number the more the image appears to be real-time.

The upper limit is determined by hardware speed and memory needed to reconstruct images. For example, having four partial images per second implies four displayed images per second. In an extreme limit, in a mathematical sense, a partial image after every view may be created, that is 900 partial images per second or 900 displayed images per second (in this example). However, for the human eye, anything beyond 25-30 images per second is not significant. Hence, in practice no more than about 20 or 25 partial images per second (900 views) may be computed to provide good quality partial images. Note that for example purposes, 900 views per second are used but this number can take on other values as needed.

As an example, assume that a total of 1800 views are collected and 900 views are required to reconstruct 1 image (Full-Scan). Then, in theory an image can be reconstructed using the view ranges (1 . . . 900), (2 . . . 901), (3 . . . 902) & so on. However, in practice, the ability of the hardware to keep up with the pace of reconstruction may be limited.

In another example, if $N_{VPR}=900$, each view block contains 225 (900/4) views. There will be a significant overlap in terms of views when reconstructing consecutive images. It is therefore not necessary to backproject $N_{VPR}$ views to reconstruction every single image. Partial images, shown in FIG. 4, may be used. Each partial image PI is formed by backprojecting only those views within the block. For example, PI(0) is a partial image formed from view block n=0, etc. Full scan images (FS) are formed by:

$$FS(k) = \sum_{i=0}^{N_{SPR}-1} PI(k-i), \text{ where } N_{SPR} > 1, k \geq N_{SPR}-1$$

Figure 4:
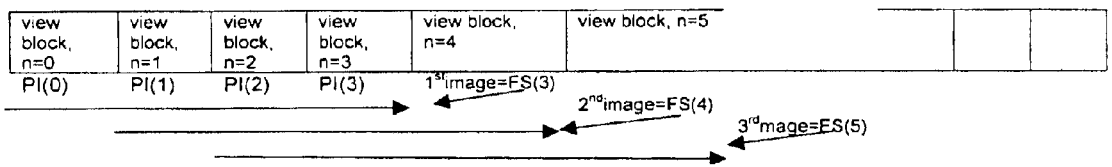
FIG. 4 is a diagram illustrating partial images.

In the example of FIG. 4,
First image=PI(0)+PI(1)+PI(2)+PI(3)=FS(3)
Second image=first image−PI(0)+PI(4)=FS(4)
Third image=second image−PI(1)+PI(5)=FS(5)
Using one adding and one subtracting operation to create the images reduces the number of operations as opposed to three additions. Here, a partial image (PI) can be computed from as small as one view. In the example, 900 consecutive (in time) partial images may be added added to give one full scan image. Computationally, using larger number of views (such as 225 in the example) to create partial images is more practical. Further, partial images may be computed using a partial scan, such as a half-scan image.

Figure 5:
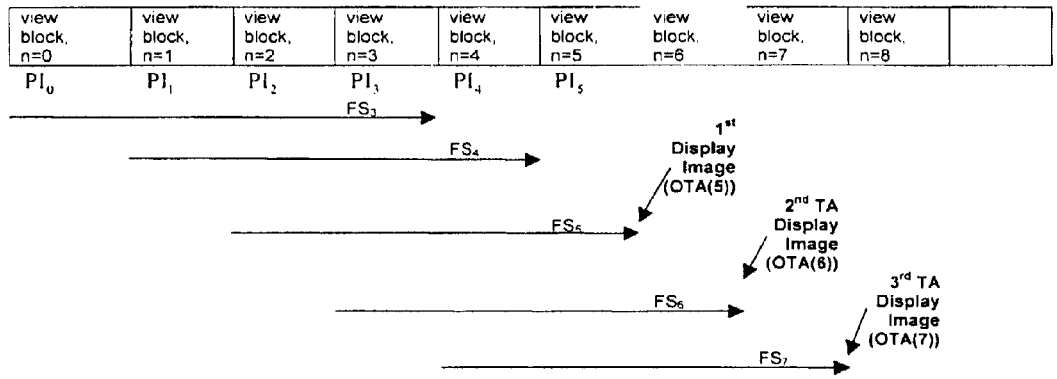
FIG. 5 is a diagram illustrating full-scan images.

According to the invention, the images may be averaged before being displayed. This is illustrated in FIG. 5. In FIG. 5, OTA denotes Overlapping Time Average. The displayed images OTA are computed in unit 12 by:

$$OTA(k) = \frac{1}{N_{OTA}} \sum_{i=0}^{N_{OTA}-1} FS(k-i),$$

where $\{N_{OTA}, N_{SPR}\} > 1$ and $k \geq N_{SPR} - 1 + N_{OTA}$

Figure 6:
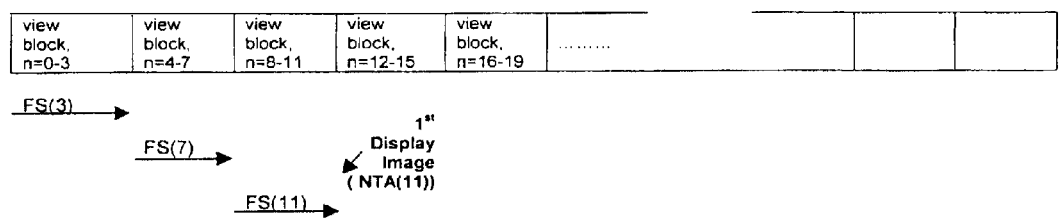
FIG. 6 is a diagram illustrating non-overlapping time images.

In this example:
First Display Image OTA(5)=average (FS(3)+FS(4)+FS(5))
Second Display Image OTA(6)=average (FS(4)+FS(5)+FS(6))
The above OTA approach works ideally when the object being scanned is stationary. However, when there is voluntary or involuntary motion, edges in the displayed image may be blurred. In a second approach to noise reduction, non-overlapping time images (NTA) are averaged. These images are smooth (less noise). This is illustrated in FIG. 6. The NTA images are computed by:

$$NTA(k) = \frac{1}{N_{NTA}} \sum_{i=1}^{N_{NTA}} FS(i \cdot N_{SPR} - 1),$$

where $N_{NTA} > 1$ and $k \geq N_{NTA} \cdot N_{SPR} - 1$ $N_{NTA}$ is defined as the number of non-overlapping time average images. For example, NTA(11)=FS(3)+FS(7)+FS(11).

Figure 7:
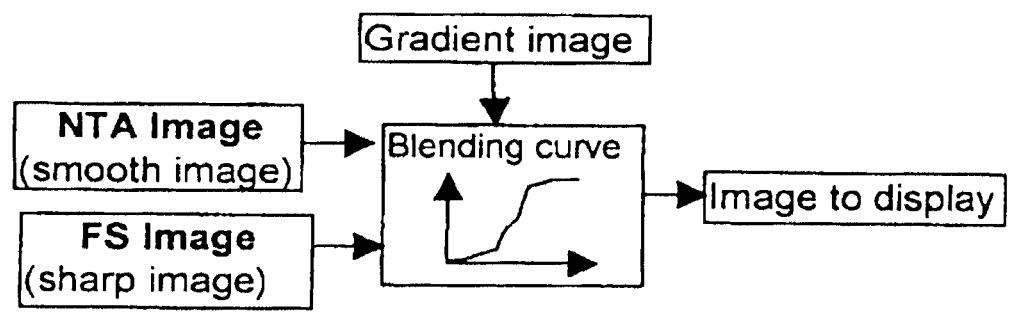
FIG. 7 is a diagram illustrating combining images.

FIG. 7 illustrates a further approach to producing an improved imaged. At the end of any view block, there are two different images that may be displayed, the NTA and FS images. The NTA image (smooth image) is combined with the FS image (sharp image) to produce an image with sharp edges without degrading the image smoothness. Here, smoothed image(11)=FS(11)++NTA(11). The symbol "++" is used to denote a blend of the images, and not an addition of corresponding voxels in the 2 images. The FS or NTA image may be defined by the newest collected view block which is 11 in the schematic of FIG. 6. Since this is 'real-time' the views in view block 12 are not being used for computation as yet, although they might be getting collected as the hardware computes FS(11), NTA(11) and FS(11)++NTA(11).

A gradient image, described in more detail below, is used to determine the contribution to each pixel in the display image from the NTA image and from the FS image. For pixels in the gradient image that have a high value (indicating an edge), the pixels in the display image will have a significantly larger contribution from the FS image (sharp image) and pixels in the display image that have a low value (indicating smooth regions) will have a larger contribution from the NTA image (smooth image).

The gradient image may be obtained as follows:

In a first approach, a difference of consecutive FS images is found, and there is $(N_{SPR}-1)/N_{SPR}$ rotation overlap.

$$Grad1_k = abs(FS(k) - FS(k-1)), \text{ where } k \geq N_{SPR}.$$

In a second approach, a difference of FS images is found, with no overlap between the images.

$$Grad2_m = abs(FS(m) - FS(m-N_{SPR})), \text{ where } m \geq 2 \cdot N_{SPR} - 1$$

In a third approach, a difference between FS and NTA images is found $$Grad3_p = abs(FS - NTA_p), \text{ where } p \geq N_{NTA} \cdot N_{SPR} - 1$$

If there is object motion (as is usually the case), scheme 1 is a better approach than scheme 2.

Figure 8:
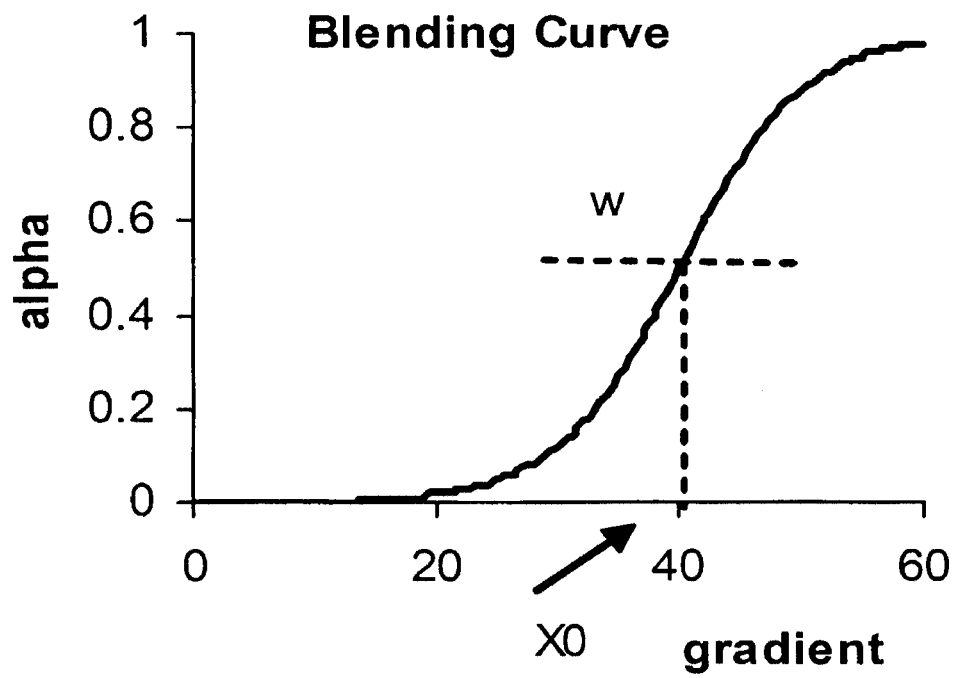
FIG. 8 is a graph illustrating a blending curve.

Once the gradient image is obtained, the gradient, FS and NTA images are blended. FIG. 8 represents one blending curve, which is represented by the following equation:

$$\frac{1}{1 + e^{-(x-x_0)/w}}$$

Here, $x_0$ and w are parameters, where $x_0$ represents the "center" of the curve and w controls the "width" of the curve.

Figure 10:
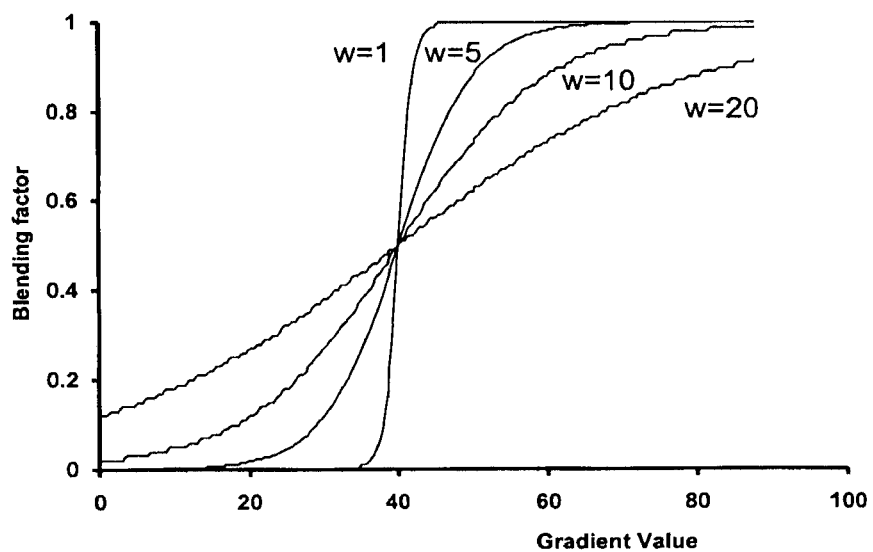
FIG. 10 is a graph of blending factor as a function of gradient value.

The parameters may be chosen by an operator or can be set automatically depending on the scan conditions and the slice position in the object being imaged. FIG. 8 shows typical values of $x_0$=40 and w=15. In FIG. 8, $x_0$ and w were selected and plugged into the above equation to obtain the curve. These values are just an example. In general, $x_o$ may be automatically selected by computing the average value of voxels in the gradient image, and w is set based on image quality. As shown in FIGS. 8 and 10, w can take on a range of values, such as between 15 and 30.

The gradient curve remains fixed for each pixel. In other words, the 'shape' of the curve does NOT depend on 'x' value, which would the gradient value at any voxel. Therefore, going from one voxel to another is tantamount to moving along the x-axis which would in turn yield a corresponding value (alpha) on the y-axis. However, the value of α for each pixel is different and this value is determined by the value of the gradient at that pixel, and is given by:

$$\frac{1}{1 + e^{-(x-x_0)/w}}$$

For each pixel in the gradient image, a new value of α is determined based on the gradient value.

At any given pixel, if the gradient value is high, a higher value of α is used such that a higher contribution to the displayed image comes from the FS (sharp) image and, on the other hand, if the gradient value is low, this means that the pixel belongs to a low frequency region and a higher contribution to the displayed image comes from the NTA (smooth) image. The following equation describes the blending to obtain the blended image BI.

$$BI_p(n) = (1-\alpha)NTA_p(n) + \alpha \cdot FS_p(n),$$

where 0<p<Number of pixels.

Figure 9:
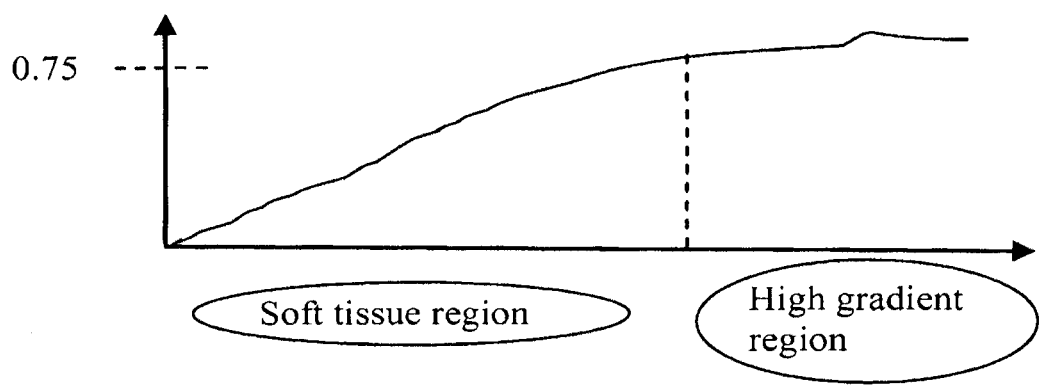
FIG. 9 is a graph illustrating gradient values in an image.

The gradient curve may be automatically selected. When the gradient image is computed, the statistics (mean, median and standard deviation) of the noise values in a soft-tissue region may be computed. On the x-axis, which represents the gradient value, the soft-tissue region and the high gradient regions will be segregated as shown in FIG. 9. A point on the gradient axis (x-axis) which results in weight=0.75 is termed as the pivot point. This pivot point is the value of 'w' (gradient value) that gives a fixed value of blending weight=0.75. Thus, using the location of pivot point with respect to the soft tissue region statistics, the blending curve can be automatically chosen. FIG. 10 illustrates different curves, for w=1, 5, 10 and 20. Curves for other values of w may be generated and used, as needed.

Figure 11:
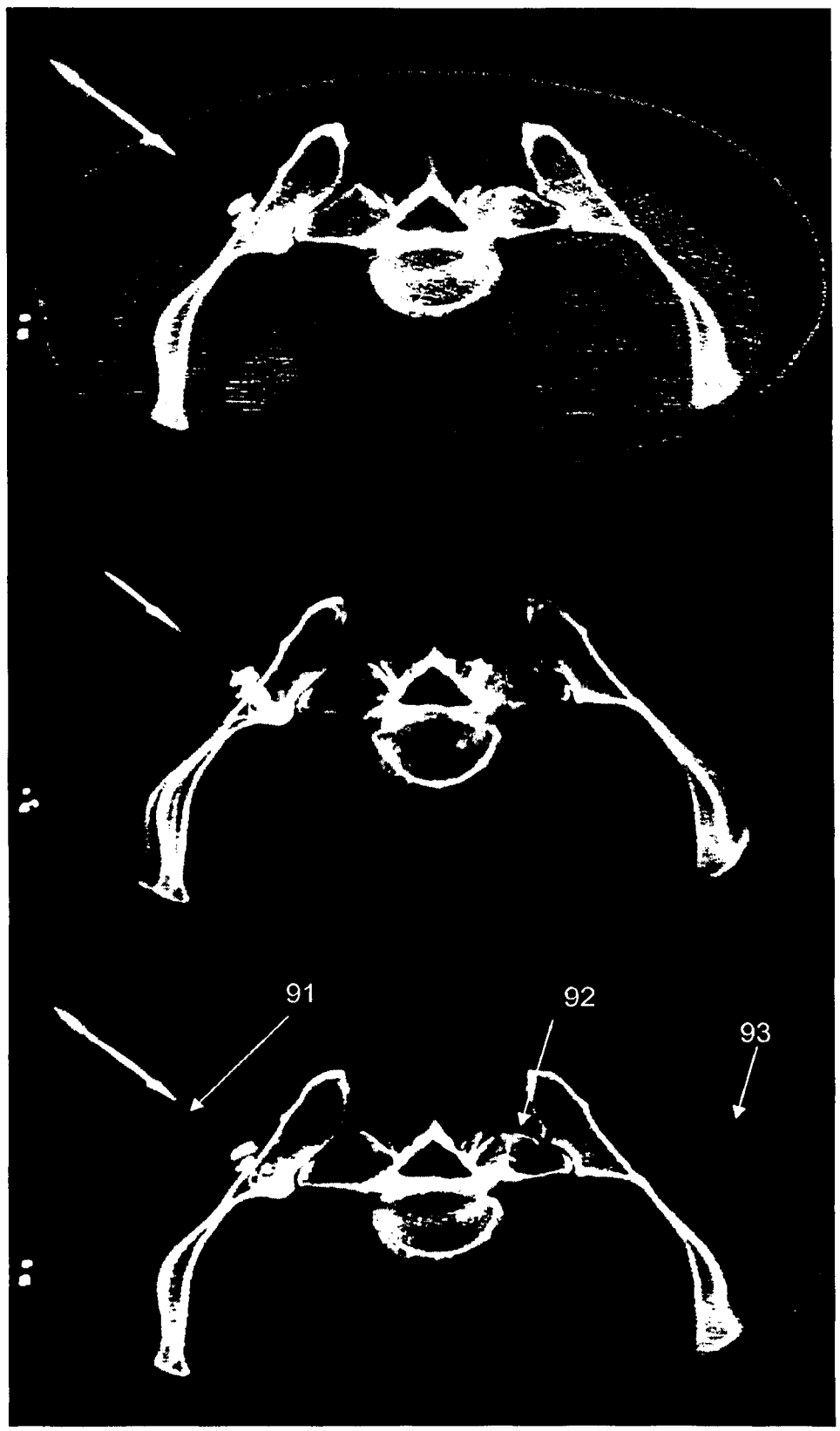
FIG. 11 shows full-scan, non-overlapping and blended images.

An example of an image obtained according to the invention is illustrated in FIG. 11. The top image is the FS image, the middle image is the NTA image and the bottom image is the blended image obtained from the above equation. Three regions are indicated in the image. Region 91 shows the sharp tip of a needle. The same needle in the NTA image is blurred. Region 92 shows that the edges in the blended image are much sharper than the NTA image. Region 93 shows how noise is reduced in the blended image compared to the FS image. Thus, according to the invention, noise can be reduced while maintaining sharpness.

A more detailed view of processing unit 12 is shown in FIG. 1A. The projection data is collected and the data for each of desired number of views is processed in processing unit 12 by processor 16 to create the partial images PI(n) and stored them in registers or memory portions 15-1 to 15-n of memory 15. Processing unit 12 also generates the FS(n) images, OTA images, NTA image, and gradient images and stores them in other registers or portions 15-o, 15-p, . . . of memory 15. Processing unit performs the blending using blending curves stored in register or memory portion 15-m, and selects the blending curve, as described above, to create the weighted images. The weighted images are also stored in 15-0, 15-p, . . . as needed. The images generated in processing unit 12 are sent to display 14 for display to the user. The images created and stored may also be transferred to other users or systems using a network such as a LAN, wireless LAN or the internet connected to the CT apparatus.

The invention may also be embodied in the form a computer-readable medium containing a stored program to cause a computer to carry out the various operations and functions described above.

Numerous other modifications and variations of the present invention are possible in light of the above teachings. It is therefore to be understood that within the scope of the appended claims, the invention may be practiced otherwise than as specifically described herein.

The invention claimed is:

1. A method for generating computed-tomography image, comprising:
    exposing an object with x-rays at a plurality of scans at a position of said object to obtain projection data at a plurality of views;
    generating first images serially in time using the projection data;
    generating second images by smoothing respective pluralities of said first images;
    generating a gradient image based on at least one of said first images;
    determining a contribution of each pixel in a display image from the first image and from the second image using the gradient image; and
    generating the display image by weight blending one of said first images and one of said second images based on the contribution.

2. A method as recited in claim 1, comprising:
    defining a plurality of said views as a view block;
    generating consecutive third images from respective consecutive view blocks; and
    generating each of said first images from a plurality of consecutive third images.

3. A method as recited in claim 2, comprising:
    using projection data from said view blocks to produce a respective plurality of said third images.

4. A method as recited in claim 2, comprising:
    generating a first one of said first images using a first plurality of said third images; and
    generating a second one of said first images by subtracting a first one of said third images from said first one of said first images and adding a next third image subsequent to said plurality of third images to said first one of said first images.

5. A method as recited in claim 1, wherein said second images comprise non-overlapping time images (NTA(k)), said first images are given by FS(k), and generating said second images comprises:

$$NTA(k) = \frac{1}{N_{NTA}} \sum_{i=1}^{N_{NTA}} FS(i \cdot N_{SPR} - 1),$$

where $N_{NTA} > 1$ and $k \geq N_{NTA} \cdot N_{SPR} - 1$ where:
    $N_{NTA}$ is a number of NTA images, and
    $N_{SPR}$ is a number of sections per rotation of said x-ray source.

6. A method as recited in claim 1, wherein first images are given by FS(k) and said gradient images are given by:

$Grad_k = abs(FS(k) - FS(k-1))$, where $k \geq N_{SPR}$, where $N_{SPR}$ is a number of sections per rotation of said x-ray source.

7. A method as recited in claim 1, wherein said first images are given by FS(m) and said gradient images are given by:

$Grad_m = abs(FS(m) - FS(m - N_{SPR}))$, where $m \geq 2 \cdot N_{SPR} - 1$ where $N_{SPR}$ is a number of sections per rotation of said x-ray source.

8. A method as recited in claim 1, wherein said first images are given by FS(k), said second images are given by $NTA_p$ and said gradient images are given by:

$Grad_y = abs(FS - NTA_p)$, where $p \geq N_{NTA} \cdot N_{SPR} - 1$ where:
    $N_{NTA}$ is a number of said second images
    $N_{SPR}$ is a number of sections per rotation of said x-ray source.

9. A method as recited in claim 1, wherein said first images are $FS_p(n)$, said second images are $NTA_p(n)$ and said display images are given as:

$Bl_p(n) = (1 - \alpha) NTA_p(n) + \alpha \cdot FS_p(n)$ where $\alpha$ is a weighting factor.

10. A method as recited in claim 9, wherein $\alpha$ is given as:

$$\frac{1}{1 + e^{-(x-x_0)/w}}.$$

11. A method as recited in claim 9, comprising:
    using a blending curve to weight said first and second images.

12. A method as recited in claim 11, comprising:
    automatically selecting said blending curve.

13. A computed-tomography apparatus, comprising:
    an x-ray source to expose an object with x-rays at a plurality of scans at a position of said object to obtain projection data at a plurality of views;
    an x-ray detector;
    a data collection unit;
    a data processing unit connected to said data collection unit; and
    a display,
    wherein:
    said data processing unit includes a memory storing x-ray projection data for a plurality of scans at a position of the object to obtain projection data at a plurality of views; and
    said data processing unit generates first images serially in time using the projection data, generates second images by smoothing respective pluralities of said first images, generates a gradient image based on at least one of said first images, determines a contribution in a display image of each pixel from the first image and from the second image using the gradient image, and generates the display image by weight blending one of said first images and one of said second images using said gradient image based on the contribution.

14. An apparatus as recited in claim 13, wherein said second images comprise non-overlapping time images (NTA(k)), said first images are given by FS(k), and said second images are generated by said data processing unit as:

$$NTA(k) = \frac{1}{N_{NTA}} \sum_{i=1}^{N_{NTA}} FS(i \cdot N_{SPR} - 1),$$

where $N_{NTA} > 1$ and $k \geq N_{NTA} \cdot N_{SPR} - 1$ where:
    $N_{NTA}$ is a number of NTA images, and
    $N_{SPR}$ is a number of sections per rotation of said x-ray source.

15. An apparatus as recited in claim 13, wherein first images are given by FS(k) and said gradient images are given by:

$$Grad_k = abs(FS(k) - FS(k-1)), \text{ where } k \geq N_{SPR},$$

where $N_{SPR}$ is a number of sections per rotation of said x-ray source.

16. An apparatus as recited in claim 13, wherein said first images are given by FS(m) and said gradient images are given by:

$$Grad_m = abs(FS(m) - FS(m - N_{SPR})), \text{ where } m \geq 2 \cdot N_{SPR} - 1$$

where $N_{SPR}$ is a number of sections per rotation of said x-ray source.

17. An apparatus as recited in claim 13, wherein said first images are given by FS(k), said second images are given by $NTA_p$ and said gradient images are given by:

$$Grad_p = abs(FS - NTA_p), \text{ where } p \geq N_{NTA} \cdot N_{SPR} - 1$$

where:
- $N_{NTA}$ is a number of said second images
- $N_{SPR}$ is a number of sections per rotation of said x-ray source.

18. An apparatus as recited in claim 13, wherein said first images are $FS_p(n)$, said second images are $NTA_p(n)$ and said display images are given as:

$$Bl_p(n) = (1-\alpha)NTA_p(n) + \alpha \cdot FS_p(n)$$

where $\alpha$ is a weighting factor.

19. An apparatus as recited in claim 18, wherein $\alpha$ is given as:

$$\frac{1}{1 + e^{-(x-x_0)/w}}.$$

20. An apparatus as recited in claim 18, comprising:
said data collection unit using a blending curve to weight said first and second images.

21. An apparatus as recited in claim 20, comprising said data collection unit automatically selecting said blending curve.

* * * * *